US00PP18868P3

(12) United States Plant Patent
Conibear

(10) Patent No.: US PP18,868 P3
(45) Date of Patent: Jun. 3, 2008

(54) ***LUPINUS* PLANT NAMED 'MANHATTAN LIGHTS'**

(50) Latin Name: ***Lupinus* hybrid**
Varietal Denomination: Manhattan Lights

(76) Inventor: Sarah Frances Conibear, West Country Nurseries Donkey Meadow, Woolsery, Bideford, Devon EX39 5QH (GB)

( * ) Notice: Subject to any disclaimer, the term of this patent is extended or adjusted under 35 U.S.C. 154(b) by 136 days.

(21) Appl. No.: 11/474,063

(22) Filed: Jun. 23, 2006

(65) Prior Publication Data

US 2007/0300341 P1 Dec. 27, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Annette H Para
(74) *Attorney, Agent, or Firm*—The Webb Law Firm

(57) ABSTRACT

'Manhattan Lights' is a new variety of *Lupinus* hybrid that exhibits numerous and large-shaped burgundy and yellow-colored flowers.

4 Drawing Sheets

Botanical classification: *Lupinus* hybrid.
Varietal denomination: 'Manhattan Lights'.

BACKGROUND OF THE INVENTION

The present invention comprises a new and distinct cultivar of *Lupinus* hybrid known by the varietal name 'Manhattan Lights'. The new variety was developed in Great Britain. The new variety is a result of cross breeding Russell Hybrid *Lupinus* Seedling #WCL 013/96 (female parent) (unpatented) and an unknown *Lupinus* male parent (unpatented). The purpose of the breeding program was to develop a cultivar that exhibited improved color, habit, and bloom form from other *Lupinus* varieties known to the breeder. The new variety is similar in growth habit to its female parent, but differs in flower color. The new variety differs from *Lupinus* hybrid 'The Governor' in flower color, closeness of flowers on spike, and growth habit. The new variety was first asexually reproduced by basal cuttings/tissue culture in Great Britain. The new variety has been trial and field tested and has been found to retain its distinctive characteristics and remain true to type through successive asexual propagations. Characteristics that distinguish the new variety from others known to the breeder include:

- Clear and intense flower color;
- Flower form — the individual bells are packed closely on the flower spike;
- Large individual bells; and
- Vigorous growth habit.

The new variety was grown in open soil with additional organic fertilizer applied. The new variety initiates and develops roots in 21 days at 15° C. A finished and flowering plant is produced in 36 weeks in a 21 cm container. The new variety exhibits sparse, but thick roots, that exhibit some branching.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
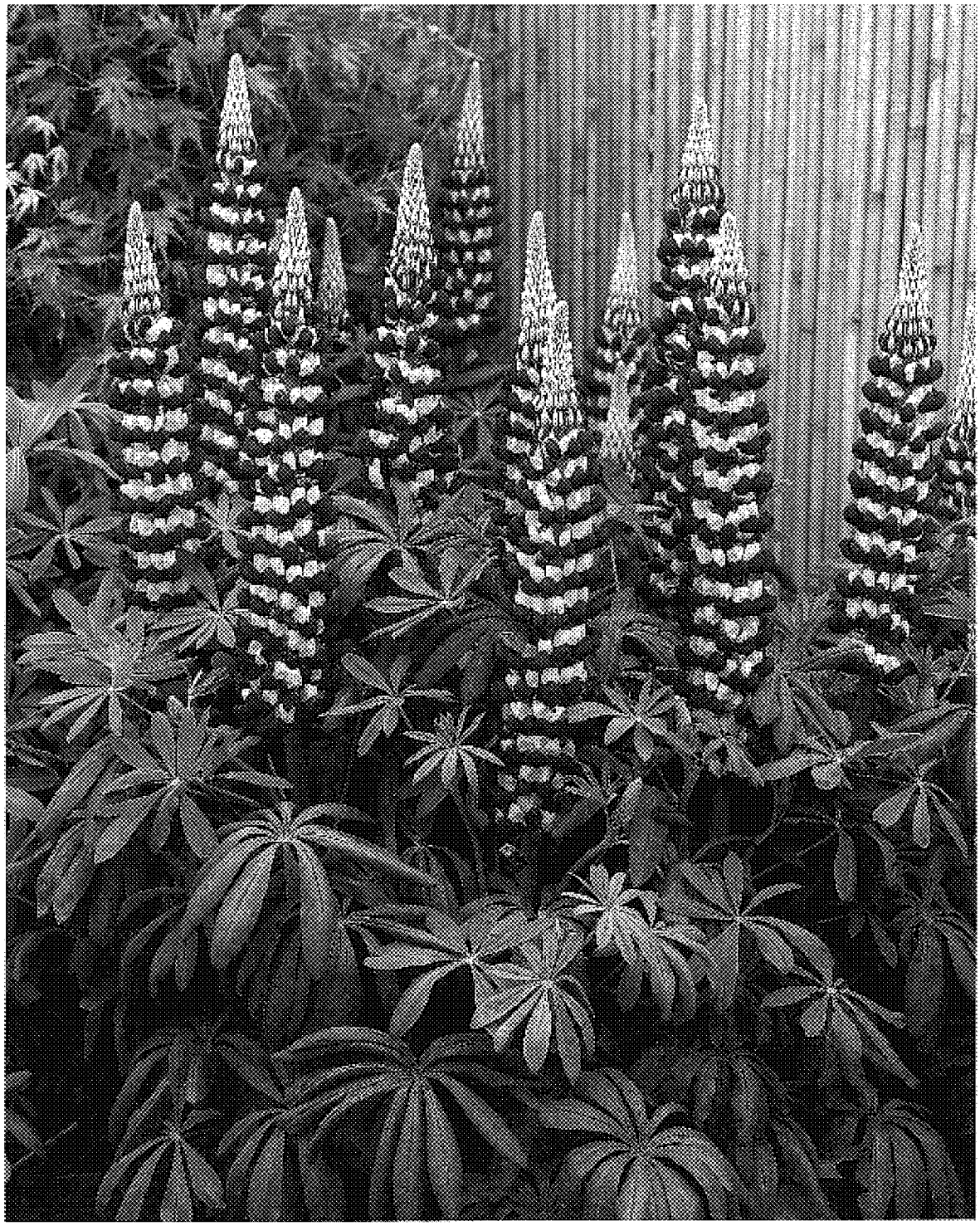
FIG. 1 is a photographic image of multiple plants of the new variety.
Figure 2:
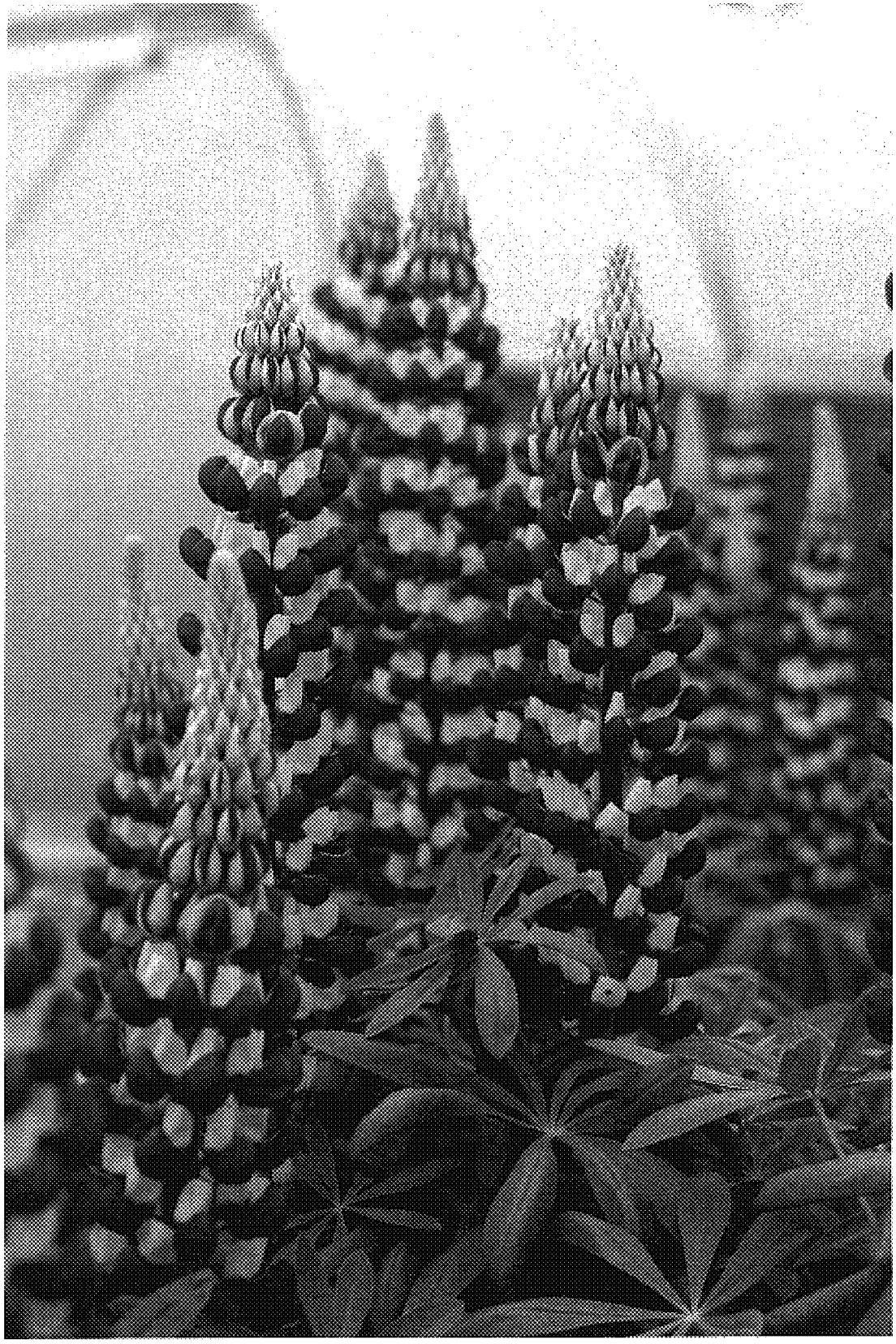
FIG. 2 is a close-up photographic image of multiple plants of the new variety.
Figure 3:
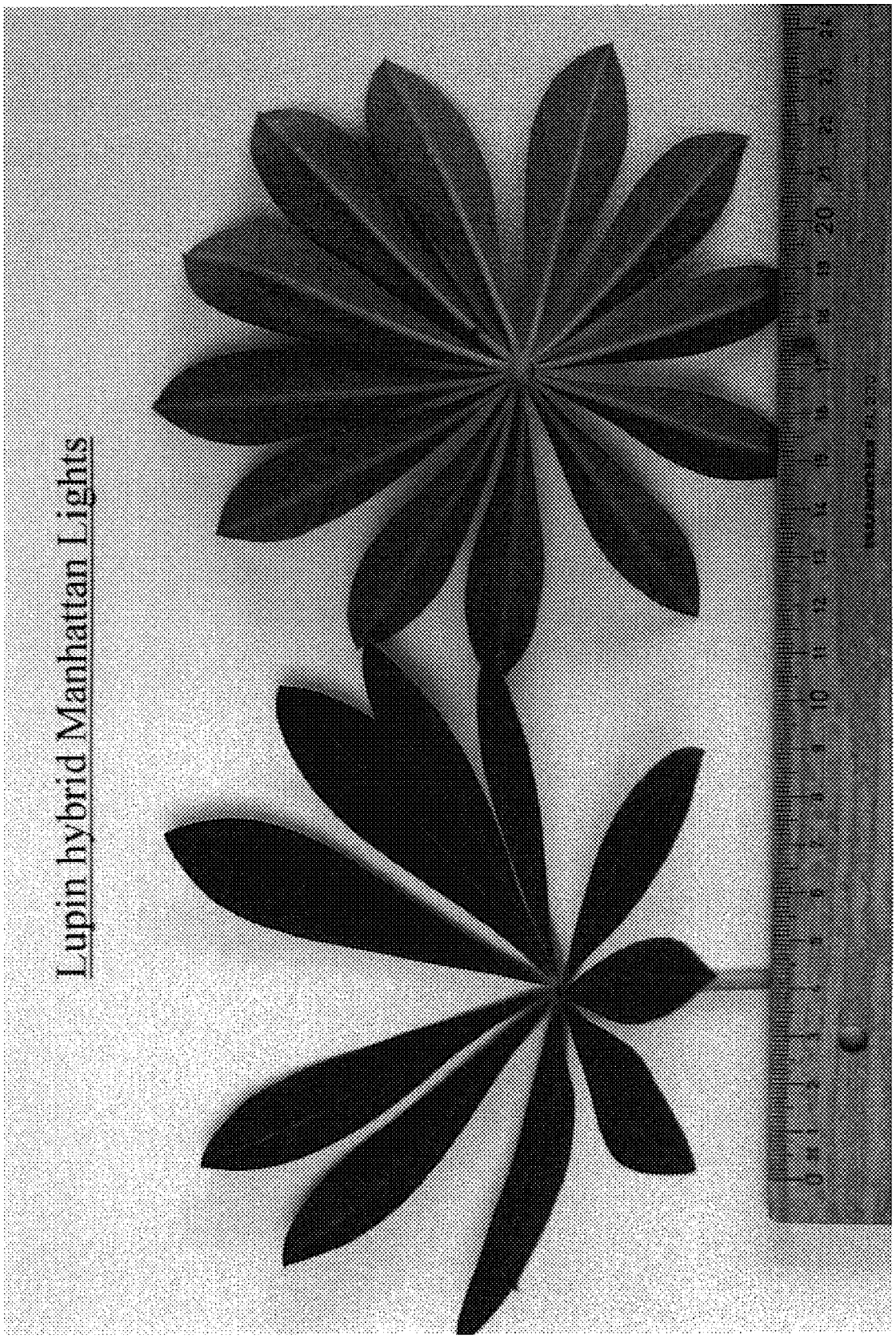
FIG. 3 is a close-up photograph of both surfaces of the leaves of the new variety.
Figure 4:
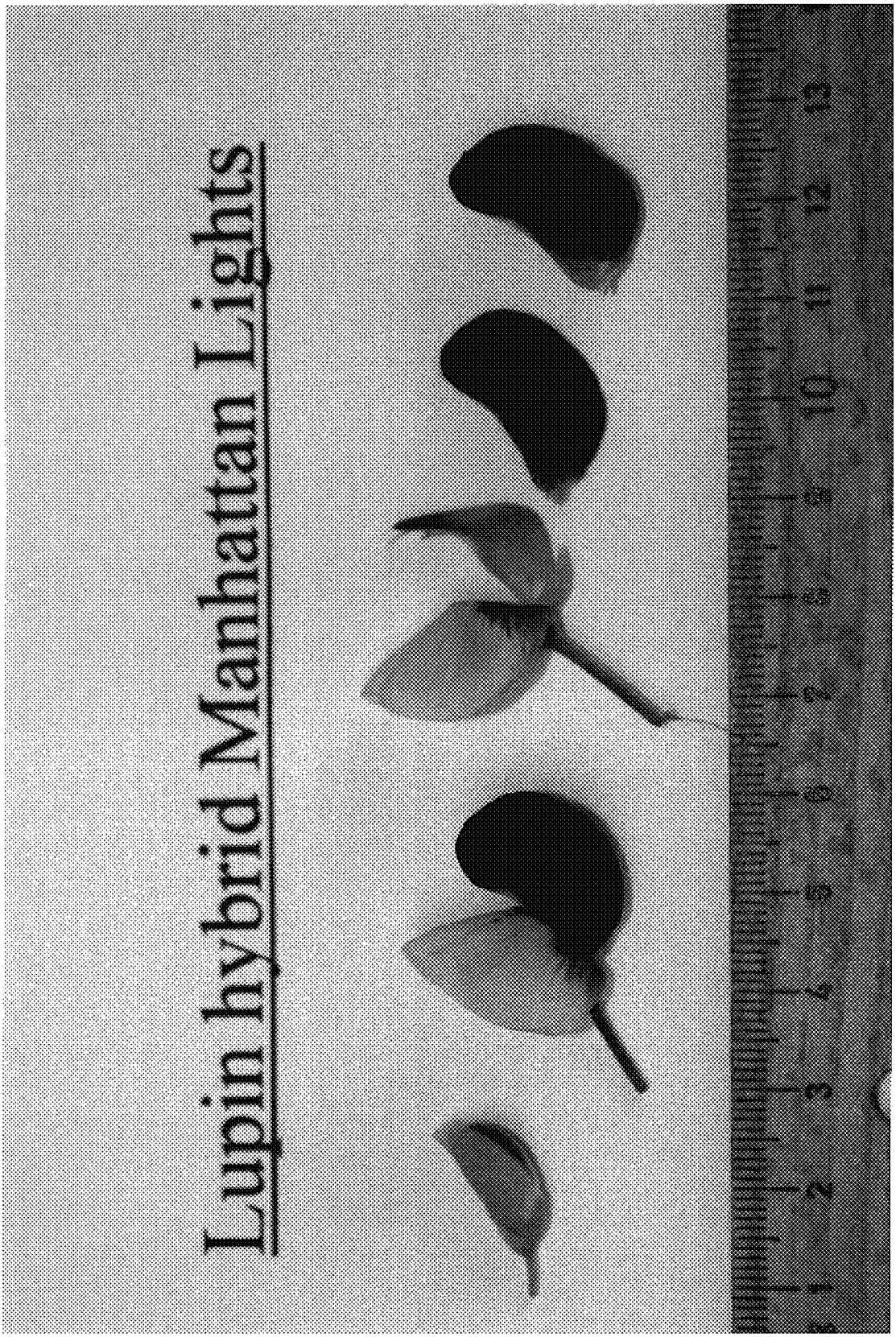
FIG. 4 is a close-up image of the petals of the new variety.

The following detailed description sets forth the characteristics of the 1 year old new cultivar. The data which defines these characteristics were collected by asexual reproductions carried out in Great Britain. The color readings were taken outside under natural daylight. Color references are primarily to the R.H.S. Colour Chart of the Royal Horticultural Society of London.

PLANT

Form: Mounded and symmetrical.
Stem:
- *Diameter.*—17 mm.
- *Color.*—144A, flushed with 70A to 71A.
- *Texture.*—Slightly hirsute, smooth with longitudinal ridges.
- *Pubescence.*—Slight to medium.

Height: 95 cm.
Vigor: Good.
Branching habit: Medium.
Lateral branches:
- *Diameter.*—11 mm.
- *Internode length.*—5 cm.
- *Texture.*—Lightly hirsute, smooth with longitudinal ridges.
- *Pubescence.*—Present.
- *Color.*—144A, flushed with 70A to 71A.

Foliage:
- *Arrangement.*—Ascending spiral.
- *Length of leaf stalk.*—Basal foliage: 25 cm. Stem foliage: 18 cm.

*Size of leaf* (*overall*).—Length: 17 cm. Width: 16 cm.
*Leaflets.*—Shape of leaflet: Oblanceolate. Number: 12. Width: 2.2 cm. Length: 8.2 cm. Shape of apex: Obtuse. Shape of base: Cuneate. Texture: Smooth and velvety. Aspect: Horizontal presentation. Margin type: Smooth; entire. Pubescence: Upper surface: None present. Lower surface: Slight. Color: Young leaflet: Upper surface: 137A with 187A edged at the tip. Lower surface: 137B/C. Mature leaflet: Upper surface: 137A with 187A suffused at the tip. Lower surface: 137B/C. Petiole: Shape: Flattened and round. Length: Basal leaf: 25 cm. Stem leaf: 18 cm. Diameter: 5 mm. Color: 144A and suffused with 70B. Venation: Central; mid-rib.

FLOWER

Bud (described when buds where just beginning to open):
*Shape.*—Napiform.
*Diameter.*—9 mm.
*Length.*—16 mm.
*Color.*—160C/D.
Natural flowering season: May through July in The Netherlands.
Flower type and habit: Spike.
*Number of flowers per spike.*—196.
*Length of spike.*—50 cm.
*Diameter of spike.*—11.8 cm.
Corolla:
*Form.*—Zygomorphic.
*Petals.*—Standard Petals: Number: 2 — fused. Length: 20 mm. Width: 13 mm. Shape: Ovate. Aspect: Parallel to spike. Margin: Smooth and entire. Wing Petals: Number: 2 — partly fused. Length: 20 mm. Width: 12 mm. Shape: Ovoid to kidney-shaped. Aspect: Tilted upward. Margin: Smooth and entire. Keel Petals: Number: 2 — fused. Length: 18 mm. Width: 8 mm. Shape: Lingulate. Aspect: Located within wing petals and pointing upwards. Margin: Smooth and entire. Texture and appearance: Smooth and satin-like. Color: When opening: Upper surface: Standard petals: 9A/B, flushed with 71B/79B at the base of the throat. Wing petals: 71A. Lower surface: Standard petals: 9B/C. Wing petals: 79A/B. Fully opened: Upper surface: Standard petals: 9A/B, flushed with 71B and 79B. Wing petals: 71A and 79A veins. Lower surface: Standard petals: 9B/C. Wing petals: 79D.
*Throat.*—Color: 4D. Texture: Smooth and satin-like.
Calyx:
*Form.*—Two unequal halves.
*Length.*—7 mm.
*Diameter.*—12 mm.
*Sepal shape.*—Elliptic.
*Sepal margin.*—Smooth and entire.
*Sepal texture.*—Smooth with slight pubescence.
*Sepal size.*—Length: 7 mm. Width: 4 mm.
Sepal color:
*Upper surface.*—149B/C.
*Lower surface.*—149B/C.
Fragrance: Slight.
Disease resistance/susceptibility: Susceptible to powdery mildew.
Temperature tolerance: Medium to good.
Lasting quality: Medium to good.

REPRODUCTIVE ORGANS

Stamens:
*Number* (*per flower*).—There are two groups. A first group with 6 stamens and a second group with 4 stamens.
*Filaments.*—Length: First group: 4 mm. Second group: 8 mm. Fused: Yes.
*Anthers.*—Shape: First group: Pencil-like. Second group: Arrow-like. Length: First group: 2 mm. Second group: 1 mm. Color: First group: 169B. Second group: 25A/B.
*Pollen.*—Color: 25A/B. Amount: Good.
Pistils:
*Length.*—12 mm.
*Style.*—Length: 12 mm. Color: 150C.
*Stigma.*—Shape: Spherical. Color: 150C.
Seed/Fruit production:
*Description of conditions when produced.*—Produced freely.
*Color.*—165A.
*Size.*—1.0 mm.
*Number.*—Approximately 2000 per plant.

I claim:

1. A new and distinct variety of *Lupinus* hybrid plant named 'Manhattan Lights' as is herein described and illustrated.

* * * * *